(12) United States Patent
Ullrich et al.

(10) Patent No.: US 6,500,988 B1
(45) Date of Patent: Dec. 31, 2002

(54) METHOD FOR PRODUCING ARYL THIOLS BY HYDROGENATING DIARYLDISULPHIDES

(75) Inventors: Friedrich-Wilhelm Ullrich, Bergisch Gladbach (DE); Helmut Fiege, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/529,875

(22) PCT Filed: Oct. 12, 1998

(86) PCT No.: PCT/EP98/06450

§ 371 (c)(1),
(2), (4) Date: Apr. 19, 2000

(87) PCT Pub. No.: WO99/20602

PCT Pub. Date: Apr. 29, 1999

(30) Foreign Application Priority Data

Oct. 22, 1997 (DE) .......................................... 197 46 512

(51) Int. Cl.$^7$ ............................................ C07C 319/06
(52) U.S. Cl. .......................................... 568/67; 568/65
(58) Field of Search ............................... 568/61, 62, 64, 568/65, 67

(56) References Cited

U.S. PATENT DOCUMENTS

| | | | | |
|---|---|---|---|---|
| 2,402,641 A | * | 6/1946 | Lazier et al. | |
| 3,326,981 A | * | 6/1967 | Levy et al. | |
| 3,331,205 A | * | 7/1967 | Laufer | |
| 3,912,757 A | | 10/1975 | Mooradian | 260/330.5 |
| 4,006,186 A | * | 2/1977 | Engels et al. | 564/440 |
| 4,636,505 A | | 1/1987 | Tucker et al. | 514/256 |
| 5,659,088 A | | 8/1997 | Fiege et al. | 568/65 |
| 5,670,504 A | | 9/1997 | Bochis et al. | 514/247 |
| 5,728,887 A | * | 3/1998 | Jacobson | 568/65 |
| 5,750,763 A | * | 5/1998 | Sugiyama et al. | 560/17 |
| 5,883,285 A | * | 3/1999 | Sugiyama et al. | 560/17 |

FOREIGN PATENT DOCUMENTS

GB 2068952 8/1981

OTHER PUBLICATIONS

Journal of Organic Chemistry by Kharasch pp. 1704–1707 1954.*

Houben–Weyl, Methoden der Organoschen Chemie, vol. IX (Month Unavailable), 1955, pp. 75–78, "Umwandlung von Disulfiden".

J. Org. Chem., vol. 24, Hotelling et al, Synthesis of Mercaptophenols and Alkyl Derivatives pp. 1598–1600 (month unavailable) 1959.

* cited by examiner

*Primary Examiner*—Jean F. Vollano
(74) *Attorney, Agent, or Firm*—Joseph C. Gil; Diderico van Eyl

(57) ABSTRACT

The invention relates to a particularly advantageous method for producing aryl thiols through the catalytic hydrogenation of diaryldisulphides. According to the invention, the hydrogenation is carried out in a basic alcoholic medium.

10 Claims, No Drawings

METHOD FOR PRODUCING ARYL THIOLS BY HYDROGENATING DIARYLDISULPHIDES

BACKGROUND OF THE INVENTION

The present invention relates to a particularly advantageous process for preparing aryl mercaptans by hydrogenation of diaryl sulphides.

Aryl mercaptans are important intermediates for preparing pharmaceutically and agrochemically active compounds (see, for example, EP-A 100 172, BE-A 887 423, US-A 3 912 757 and WO 96/25936).

A useful process for preparing aryl mercaptans consists in the reaction sequence of the reduction of arylsulphonyl chlorides with sodium sulphite to arylsulphinic acid salts, further reduction with sulphuric acid to the diaryl disulphide and finally cleavage of the disulphide with sodium borohydride (DE-A 44 20 777). Unsatisfactory here is the cleavage of the disulphide with sodium borohydride which does proceed in good yield, but which requires sodium borohydride, a reagent which is difficult to prepare and thus expensive.

Catalytic hydrogenating cleavages of diaryl disulphides have also been described; however, they always proceed at high temperatures and pressures or require other disadvantageous measures. Thus, according to J. Org. Chem. 24, 1598 (1959), the reaction is carried out in toluene using an $MoS_2$-aluminium oxide catalyst at 140° C. and 124 bar. DE-A 17 68 421 describes this hydrogenation with palladium contacts and Raney cobalt at 160 to 200° C. and 150 bar. According to JP-A (Japanese Published Specification) 60/199 871, the hydrogenation is carried out using Raney nickel in a heterogeneous solvent system comprising two phases, i.e. an aqueous/alkaline and a water-insoluble organic phase.

If these processes are carried out at lower pressures and lower temperatures, conversion is incomplete (see Comparative Examples 1 and 2).

We have now found a process for preparing aryl mercaptans by catalytic hydrogenation of diaryl disulphides which is characterized in that the hydrogenation is carried out in a basic alcoholic medium.

DESCRIPTION OF THE INVENTION

According to the process according to the invention, it is possible to prepare, for example, aryl mercaptans of the formula (I)

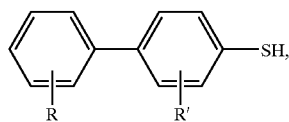

in which
R and R' independently of one another each represent hydrogen, $C_1$–$C_6$-alkyl, $C_1$–$C_6$-alkoxy or halogen, from the corresponding diaryl disulphides of the formula (II)

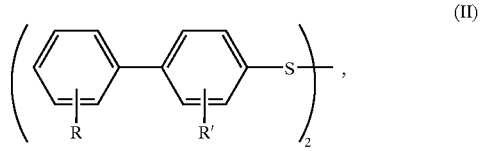

in which
R and R' are as defined in formula (I).

In the formulae (I) and (II), R and R' independently of one another preferably represent hydrogen, methyl, ethyl, methoxy, ethoxy, fluorine or chlorine. Particularly preferably, R and R' represent hydrogen.

The diaryl disulphides required as starting materials, in particular those of the formula (II), can be obtained by various routes, for example according to DE-A 44 20 777. Of particular interest here is a process in which S-(4-biphenyl)-sulphinic acid or salts thereof are reacted with an aqueous bisulphite solution at a pH of 2 to 7, thus giving the corresponding S-(4-biphenyl)-thiosulphuric acids or salts thereof, which are heated in the presence of a strong aqueous acid. This process is described in more detail in another patent application which was submitted simultaneously by the same applicant.

Suitable solvents for forming the alcoholic medium required according to the invention are, for example, aliphatic $C_1$–$C_5$-alcohols, which may be straight-chain or branched. They can be primary, secondary or tertiary alcohols. Preference is given to methanol, ethanol and isopropanol. The alcoholic medium may optionally also comprise water, for example up to 20% by weight, preferably up to 10% by weight. It is therefore, for example, not necessary to employ the diaryl disulphide in dry form. It can be used just as well in the form of the water-moist product obtained in its preparation. It is also possible to use mixtures of different alcohols as alcoholic medium.

Based on 1 mol of diaryl disulphide, it is possible to employ, for example, 200 to 10,000 ml of alcohol. This amount is preferably 500 to 5000 ml.

Suitable agents for generating a basic character in the alcoholic medium are, for example, alkali metal hydroxides, alkali metal carbonates or alkali metal alkoxides, in particular alkali metal $C_1$–$C_4$-alkyl alkoxides or the corresponding alkaline earth metal compounds. Preference is given to alkali metal hydroxides, in particular to sodium hydroxide and potassium hydroxide.

Based on 1 mol of diaryl disulphide, it is possible to employ, for example, 0.5 to 5 equivalents of base. This amount is preferably 1.5 to 2.5 equivalents.

Suitable catalysts for the hydrogenation according to the invention are, for example, metals of the VIII transition group of the PTE, in particular nickel and palladium. Such metals can be used as such or as metal compounds. Metals or metal compounds can optionally be arranged on carrier materials such as activated carbon, aluminium oxide, alkaline earth metal carbonate or alkaline earth metal sulphate. The catalysts may be doped with other metals or metal compounds, for example those of the $4^{th}$ or $8^{th}$ transition group of the PTE. They can also be present in the form of skeleton catalysts, for example in Raney form. Preferred catalysts are palladium on carbon, palladium black, Raney nickel and Raney nickel which is doped with cobalt and/or iron. Particular preference is given to Raney nickel.

The catalytic hydrogenation according to the invention can be carried out, for example, at temperatures of 20 to 200° C. and pressures of up to 50 bar. Preference is given to temperatures of 40 to 150° C. and pressures of up to 25 bar, in particular to temperatures of 60 to 120° C. and pressures of up to 15 bar.

Work-up of the reaction mixture which is present after the hydrogenation according to the invention can be carried out, for example, by cooling, for example to 20 to 65° C., separating off the catalyst, for example by filtration, treating the resulting alcoholic solution of the aryl mercaptan which has been prepared with acid and, if appropriate, water and then filtering off and drying the precipitated product.

Using the process according to the invention, it is possible to obtain aryl mercaptans, in particular diaryl mercaptans of the formula (I), in good yields and purities.

The process according to the invention has surprising advantages. Thus, it does not require any reagents which are difficult to prepare. It can be carried out at lower temperatures and in particular at lower pressures than other processes, which means less expenditure on apparatus and handling. Finally, a complicated procedure with two liquid phases present side by side is avoided. Particularly surprising here is the fact that, from Houben-Weyl, Methoden der organischen Chemie, Volume IX, p. 77 (1955), it is known that in basic medium disulphides undergo disproportionation into sulphinates and thiols. Hitherto, it was attempted to suppress this undesirable reaction by using water-immiscible solvents. Surprisingly, it was found that this is not necessary.

The invention is further described in the following illustrative examples in which all parts and percentages are by weight unless otherwise indicated.

EXAMPLES

Example 1

In a 0.3 l stainless-steel autoclave, 0.1 mol of bis-(4-diphenyl) disulphide were suspended in a solution of 8 g of sodium hydroxide in 220 g of ethanol and admixed with 1 g of Raney nickel. The batch was hydrogenated at 80° C. using 10 bar of hydrogen. After hydrogen uptake had ended, the mixture was cooled and vented. The catalyst was filtered off at 60° C. and the mixture was then diluted with 150 ml of water, and the pH was adjusted to 1 using 20 ml of aqueous hydrochloric acid (37% by weight strength). The precipitated product was filtered off with suction and washed with water. Drying gave 35.1 g of 4-mercaptodiphenyl with a content of 95.7% by weight. This corresponds to a yield of 90.2% of theory.

Comparative Example 1

The hydrogenation was carried out as in Example 1, but without addition of sodium hydroxide. There was no uptake of hydrogen. When the reaction mixture was worked up, only the starting material was recovered.

Comparative Example 2 (analogous to JP-A (Japanese Published Specification) 60/199 871)

In a two-phase system of 100 ml of toluene and a solution of 8 g of sodium hydroxide in 150 ml of water, 38.4 g of bis-(4-diphenyl) disulphide were suspended. The mixture was admixed with 1 g of Raney nickel and the batch was hydrogenated at 80° C. and 10 bar. After 4 hours, hydrogen uptake ceased. The mixture was cooled and the batch was vented.

In addition to the catalyst, the reaction mixture also contained unreacted bis-(4-diphenyl) disulphide as a solid. After concentration, bis-(4-diphenyl) disulphide was also found in the toluene phase. The aqueous phase was acidified using 37% by weight strength aqueous hydrochloric acid, and the precipitated product was filtered off with suction and washed with 100 ml of water. Drying gave 21.4 g of 4-mercaptodiphenyl with a content of 93.6% by weight. This corresponds to a yield of 53.8% of theory.

Example 2

Hydrogenation was carried out as in Example 1, but using methanol instead of ethanol as solvent. This gave 37.1 g of 4-mercaptodiphenyl with a content of 97.1% by weight. This corresponded to a yield of 96.7% of theory.

Example 3

Hydrogenation was carried out as in Example 1, but using isopropanol instead of ethanol as solvent. This gave 31.8 g of 4-mercaptodiphenyl with a content of 81.7% by weight. This corresponded to a yield of 69.8% of theory.

Example 4

189 g of bis-(4-diphenyl) disulphide was prepared as described in Example 5, but used for the hydrogenation in the form of the moist filter cake (276 g). To this end, the moist filter cake was suspended in 800 g of ethanol and admixed with 44 g of sodium hydroxide and 5.5 g of Raney nickel. The mixture was heated to 80° C. in an autoclave, and a hydrogen pressure of 10 bar was applied. Hydrogen uptake ceased after 4 hours. The batch was cooled and vented. The catalyst was filtered off at 60° C. and the filtrate was then acidified using 840 ml of 5.4% by weight strength aqueous hydrochloric acid. On acidification, the product precipitated out. The product was filtered off with suction, washed with 250 ml of water and dried. This gave 178.8 g of a white powder of melting point 110 to 112° C. The 4-mercaptodiphenyl content was 91.8% by weight (determined iodometrically). This gave a yield of 80.1% of theory, based on the diphenyl-4-sulphonyl chloride originally employed.

Example 5

(Preparation of bis-(4-diphenyl) disulphide—not according to the invention)

400 ml of 39% by weight strength aqueous bisulphite liquor and 550 ml of water were initially charged with 125 ml of aqueous sodium hydroxide solution (45% by weight strength) and admixed with 2.2 g of triethylbenzylammonium chloride. The mixture was heated to 60° C. In the course of 1 hour, 289.5 g of diphenyl-4-sulphonyl chloride (96% by weight strength) were introduced, and the pH of the reaction mixture was at the same time maintained at 8 by metering in 45% by weight strength aqueous sodium hydroxide solution. During the three hours of extra stirring time, the pH was likewise kept constant by metering in sodium hydroxide solution. In a 3 l enamel autoclave, the reaction mixture was then admixed with 80 ml of sulphur dioxide and heated at 130° C. for 3 hours. The batch was stirred for 6 hours at 130° C. and a pressure of 4.4 to 6.9 bar. The batch was subsequently cooled to room temperature and vented. The resulting suspension was filtered off with suction. The filter cake was dried. This gave 237.4 g of solid with a bis-(4-diphenyl) disulphide content of 78.3%. This corresponds to a yield of 91.2% of theory.

Although the present invention has been described in detail with reference to certain preferred versions thereof, other variations are possible. Therefore, the spirit and scope of the appended claims should not be limited to the description of the versions contained therein.

What is claimed is:

1. A process for preparing aryl mercaptans by catalytic hydrogenation of diaryl disulphides wherein the hydrogenation is carried out in a basic alcoholic medium.

2. The process according to claim 1, wherein aryl mercaptans of the formula (I)

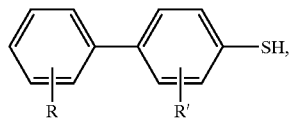

in which
R and R' independently of one another each represent hydrogen, a $C_1$–$C_6$-alkyl group, a $C_1$–$C_6$-alkoxy group or a halogen,
are prepared from the corresponding diaryl disulphides of the formula (II)

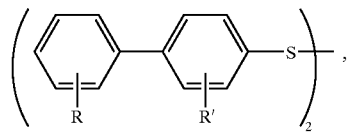

in which
R and R' are as defined in formula (I).

3. The process according to claim 1, wherein the solvents used for forming the alcoholic medium are aliphatic $C_1$–$C_5$-alcohols.

4. The process according to claim 1, wherein the alcoholic medium comprises up to 20% by weight of water.

5. The process according to claim 1, wherein the agents used for generating a basic character in the alcoholic medium are alkali metal hydroxides, alkali metal carbonates or alkali metal alkoxides or the corresponding alkaline earth metal compounds.

6. The process according to claim 1, wherein 0.5 to 5 equivalents of base are employed per mole of diary disulphide.

7. The process according to claim 1, wherein the catalysts used are metals of the VIII transition group of the Periodic Table of Elements.

8. The process according to claim 1, wherein the catalytic hydrogenation is carried out at temperatures of from 20 to 200° C. and pressures of up to 50 bar.

9. The process according to claim 1, wherein the catalytic hydrogenation is carried out at 40 to 150° C. and pressures of up to 25 bar.

10. The process according to claim 1, wherein the reaction mixture which is present after the catalytic hydrogenation has been carried out is worked up in that it is cooled, the catalyst is separated off, the resulting alcoholic solution of the aryl mercaptan which has been prepared is treated with acid and the precipitated product is filtered off and dried.

* * * * *